US006004191A

United States Patent [19]

Schur et al.

[11] Patent Number: 6,004,191

[45] Date of Patent: Dec. 21, 1999

[54] PARTICULATE MATTER DELIVERY DEVICE

[75] Inventors: Henry B. Schur; John E. Trafton, both of Hallandale, Fla.

[73] Assignee: Simplex Medical Systems, Inc., Hallandale, Fla.

[21] Appl. No.: 08/863,857

[22] Filed: May 27, 1997

Related U.S. Application Data

[63] Continuation-in-part of application No. 08/517,379, Aug. 21, 1995, abandoned, and application No. 08/746,737, Nov. 15, 1996, abandoned.

[51] Int. Cl.[6] ..................... B24C 5/04

[52] U.S. Cl. ..................... 451/90; 451/101

[58] Field of Search ..................... 451/38, 39, 101, 451/102, 90, 99

[56] References Cited

U.S. PATENT DOCUMENTS

| | | | |
|---|---|---|---|
| 2,441,441 | 5/1948 | Paasche | 451/90 |
| 2,725,684 | 12/1955 | Crowe | 451/90 |
| 3,631,631 | 1/1972 | Greenstein | 451/90 |
| 4,475,370 | 10/1984 | Stark et al. | 451/89 |
| 4,941,298 | 7/1990 | Fernwood et al. | 451/99 |
| 5,123,206 | 6/1992 | Woodson | 451/39 |

*Primary Examiner*—Robert A. Rose
*Attorney, Agent, or Firm*—Robert J. Van Der Wall

[57] ABSTRACT

Disclosed is an improved apparatus for delivery of pressurized particulate matter against a surface or target to abrade, etch, erase, cut, penetrate, smooth, clean, polish and/or harden the surface or target. The most important use to which the present invention is adapted is use by dentists and oral hygienists to very effectively clean teeth, employing a particulate matter such as aluminum oxide, while at the same time having no effect on soft tissue such as the gums. This is accomplished using a prefilled, sealed, and disposable fluidizing chamber and cannula assembly that avoids contamination and which has already been approved by the FDA for dental use. Included is a fluidizing chamber having a discharge end of an inlet tube that is disposed below or overlaps the intake end of the cannula such that the discharge of the inlet tube blows the particulate matter into the fluid above the intake end of the cannula, thereby suspending it therein, without clogging. The invention further provides for a custom designed double acting safety check valve to prevent backflow of particulate matter in the event of a drop in pneumatic pressure, and also to prevent excessive pressure from reaching the fluidizing chamber and cannula in the event of a pressure surge. Another feature of the invention includes a tapered nozzle and optionally bent cannula. The check valve attaches to the pre-existing pneumatic pressure line of a dental office pedestal.

13 Claims, 2 Drawing Sheets

PARTICULATE MATTER DELIVERY DEVICE

This application is a Continuation-In-Part of U.S. application Ser. Nos. 08/517,379 filed on Aug. 21, 1995, and 08/746,737 filed on Nov. 15, 1996, both of which are now abandoned, which are incorporated by reference. However, changes that included deletions from the aforementioned parent applications have necessitated a change in the inventive entity.

BACKGROUND OF THE INVENTION

1. Field of the Invention

This invention relates to delivery devices, and in particular to an improved apparatus for delivery of pressurized particulate matter against a surface or target to abrade, etch, erase, cut, penetrate, smooth, clean, polish and harden the surface or target.

BACKGROUND OF THE INVENTION

While a number of generalized applications for the present invention are mentioned above, one specific use to which the present invention is adapted is use by dentists and oral hygienists to clean teeth, particularly in preparation to adhere other materials to a tooth, such as a filling. The present invention is extremely well adapted to this application because it delivers a very effective cleaning capability, employing a particulate matter such as aluminum oxide, while at the same time having no effect on soft tissue such as the gums.

The major aspect of the present invention is a prefilled, sealed, and disposable fluidizing chamber and cannula assembly that avoids contamination and which has already been approved by the FDA for dental use. Earlier designs of pressurized particulate matter delivery devices have demonstrated there can be difficulty with clogging in the fluidizing chamber and/or the delivery tube. The present invention is partially directed to an improved internal structure of the fluidizing chamber which produces effective fluidization without clogging. It further provides for a custom designed double acting safety check valve to prevent backflow of particulate matter in the event of a drop in pneumatic pressure, and also to prevent excessive pressure from reaching the fluidizing chamber and delivery tube in the event of a pressure surge. Another feature of the invention includes a tapered nozzle and optionally bent particle delivery cannula. The custom designed double acting safety check valve aspect of the invention is designed to attach to the pneumatic pressure line of a dental office pedestal, operated by a foot pedal. This disposable fluidizing chamber and cannula assembly is extremely lightweight and is removably connected to the check valve.

Examples of prior known devices include that described in U.S. Pat. No. 4,941,298 to Fernwood, which discloses a rear-reservoir micro sandblaster. The Fernwood patent has numerous problems including costly to dispose, special training for set up and use, cannot deliver varying sizes of particles, contaminated after each use, must be completely sterilized after each use. Other known devices with similar problems are the Microetcher™ and the Handiblaster™ available from Mirage/Chameleon Dental Products, Inc.

SUMMARY OF THE INVENTION

The primary object of the present invention is to provide a particulate matter delivery device that includes an FDA approved prefilled, sealed, and disposable fluidizing chamber and cannula that avoids contamination. Prefilling, sealing, and disposability are key aspects to assurances that materials used in a patient's mouth are sanitary since the manufacturing facility has complete control over the sterility of the inventive device and the particulate matter with which it is charged in the manufacturing process.

Another important object of the present invention is to provide a particulate matter delivery device that includes an improved internal structure of the fluidizing chamber which produces effective fluidization without clogging.

One more important object of the present invention is to provide a particulate matter delivery device wherein the prefilled, sealed, and disposable fluidizing chamber and cannula assembly is removably connected to a custom designed double acting safety check valve, which acts to both prevent backflow to the pneumatic pressure line of a dentist's pedestal in the event of a pressure drop and also prevents pressure surges from reaching the fluidizing chamber, and the patient's mouth.

A related object of this invention is to provide a particulate matter delivery apparatus wherein the custom designed double acting safety check valve is removably attached to the pneumatic pressure line of a dental office pedestal, operated by a foot pedal.

A further object of this invention is to provide a device for delivery of a fluid particle stream using a cannula with a tapered nozzle to accelerate particle velocity.

An additional object of this invention is to provide a particulate matter delivery apparatus that is very lightweight to make it easy for a dentist or oral hygienist to use.

One more object of the invention is to provide an effective, safe, sanitary, FDA approved, easy to use dental cleaning device that requires essentially no capital investment by the dentist because it employs a pneumatic pressure line already found on a dentist's pedestal, uses a small lightweight check valve, and a small lightweight fluidizing chamber and cannula assembly that is disposable.

A preferred embodiment includes a fluidizing chamber for mixing fluid and particulate matter together by suspending the latter in the former, and a cannula tube having a particle accelerating tapered nozzle extending outside the fluidizing chamber, wherein the cannula tube delivers pressurized particulate matter from the fluidizing chamber to a surface or target at a high velocity.

The fluidizing chamber incorporates a simple yet extremely effective internal structure to accomplish the suspension of the particulate matter in the fluid, usually air. It is merely comprised of a discharge end of an inlet tube that is disposed below the intake end of the cannula or overlaps it. Both the inlet tube and cannula tube are preferably insert molded into the adjoining members of the fluidizing chamber structure. The effect is that the discharge of the inlet tube blows the particulate matter into the fluid above the intake end of the cannula, thereby suspending it therein, without clogging.

The members of the fluidizing chamber structure are comprised of a barrel, to which the cannula is preferably insert molded, and a barrel end cap, to which the inlet tube is preferably insert molded. The barrel end cap preferably has internal threads which rotate about and engage mateable threads on the top of the barrel of the fluidizing chamber. This structure allows, in an alternative embodiment, for the inventive to be recharged with particulate matter, but in the preferred embodiment, the fluidizing chamber is prefilled, sealed, and disposable. Sealing is accomplished by gluing or otherwise preventing relative movement between the mating threads of the fluidizing chamber barrel and its barrel end cap after the fluidizing chamber has been charged with particulate matter. In the preferred embodiment, the manufacture, charging and sealing is all accomplished under sanitary conditions because the product is going to be used in a patient's mouth.

Another important feature of the preferred embodiment is the custom designed double acting safety check valve which is disposed between the prefilled, sealed, and disposable fluidizing chamber and the pneumatic pressure line of a dental office pedestal. This check valve primarily acts to prevent particulate matter from being drawn back in to the pneumatic pressure line in the event of a sudden drop in pressure, but will also will seal off the inlet tube into the fluidizing chamber in the event of a pressure surge such as may occur with a regulator failure or an unregulated runaway compressor.

One more feature of the invention is the use of a particle accelerating tapered nozzle at the discharge end of the cannula. This increases the velocity of the particles exiting from the cannula discharge orifice.

Further objects and advantages of this invention will be apparent from the following detailed description of a presently preferred embodiment which is illustrated schematically in the accompanying drawings.

DESCRIPTION OF THE PREFERRED EMBODIMENTS

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Figure 1:
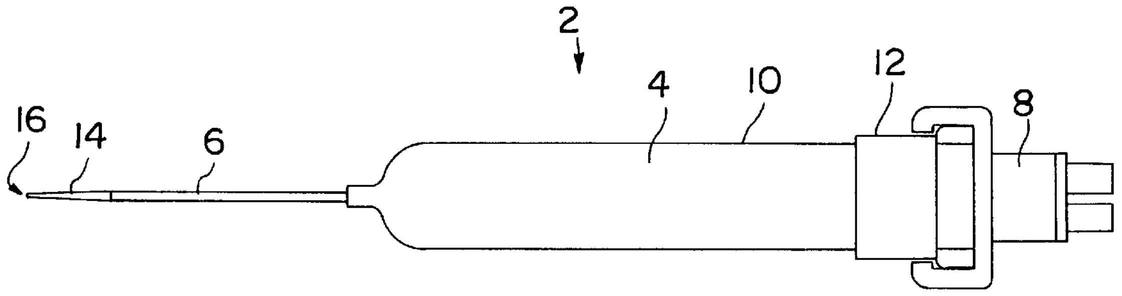
FIG. 1 is a plan view of the improved particulate matter delivery device.

FIG. 1 is a plan view of the improved particulate matter delivery device 2, having a fluidizing chamber 4, cannula 6, and double acting check valve 8. The fluidizing chamber 4 is comprised of barrel 10, and barrel end cap 12. Cannula 6 preferably includes a tapered nozzle 14 to accelerate particle velocity toward the target (not shown). Cannula 6 terminates, of course, with a discharge orifice 16.

Figure 2:
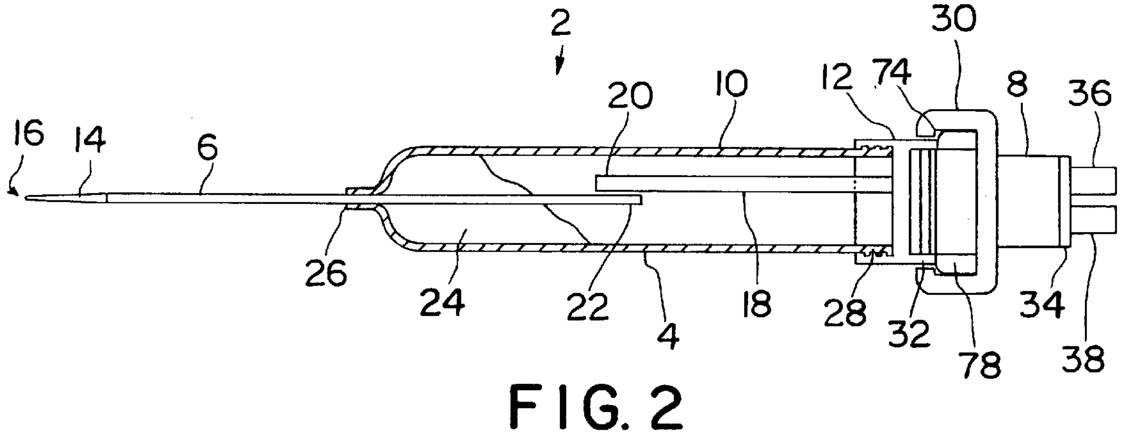
FIG. 2 is a partial cross-sectional view of the improved particulate matter delivery device of FIG. 1, showing the interior structure of the fluidizing chamber.

FIG. 2 is a partial cross-sectional view of the improved particulate matter delivery device 2 of FIG. 1, showing the interior structure of the fluidizing chamber 4. Inlet tube 18 having discharge end 20 is shown overlapping the intake end 22 of cannula 6 to achieve the suspension of particulate matter in fluid such as air. Since the improved particulate matter delivery device 2, when in use, is usually held erect with the cannula 6 generally below the fluidizing chamber 4, the particulate matter 24 will generally then be resting at the cannula end of the barrel 10. It is for that reason that the above description refers to the internal structure of the fluidizing chamber as having a discharge end of an inlet tube that is disposed "below" the intake end of the cannula 6. Check valve jaws 30 and valve end cap 12 locking hub end 32 and barrel end cap bulges 78 interconnect. Cannula 6 is tightly held in barrel aperture 26. It is preferably insert molded thereat but also may be glued, press fitted or the like. Elsewhere, barrel end cap 12 is shown attached to barrel 10 at mateable threads 28. Also seen are double acting check valve 8, check valve jaws 30, which interconnect with locking hub end 32 at the top end of barrel end cap 12, gasket 34, guide pin 36 and pneumatic pressure line connector 38.

Figure 3:
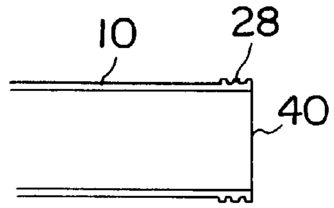
FIG. 3 is a broken cross sectional view of the top end of the barrel member of the fluidizing chamber showing the threaded end thereof.

FIG. 3 is a broken cross sectional view of the top end 40 of the barrel member 10 of the fluidizing chamber 4 showing the mateable threads 28.

Figure 4:
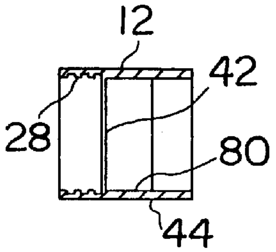
FIG. 4 is a cross-sectional view of the barrel end cap member showing mating internal threads for attachment to corresponding threads on the top of the barrel.

FIG. 4 is a cross-sectional view of the barrel end cap 12 showing mating internal threads 28, for attachment to corresponding threads on the top of the barrel, and barrel end cap aperture 42 into which is placed inlet tube 18 as seen in FIG. 2. Inlet tube 18 is placed in barrel end cap aperture 42 preferably during the molding process, i.e., is insert molded. Alternatively inlet tube 18 may be glued or press fitted into barrel end cap aperture 42. Finally, barrel end cap 12 includes barrel end cap flats 44 as more clearly seen in FIG. 5 and O-ring bearing internal surfaces 80.

Figure 5:
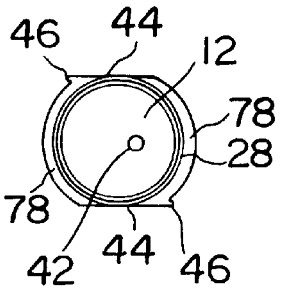
FIG. 5 is a end view of the barrel end cap member of the fluidizing chamber showing eccentric position of the opening into which the inlet tube is placed to accommodate the fact that the discharge end of an inlet tube is disposed below the intake end of the cannula, which is concentric with the barrel. This Figure also shows the alternating barrel end cap flats and bulges of the locking hub end.

FIG. 5 is a end view of the barrel end cap 12 of the fluidizing chamber 4 showing the eccentric position of the barrel end cap aperture 42, which is necessitated by the overlapping configuration of the inlet tube 18 and the barrel concentric cannula 6 as seen in FIG. 2. Also seen barrel end cap flats 44, barrel end cap bulges 78, rotation stops 46, and, in phantom, mateable threads 28.

Figure 6:
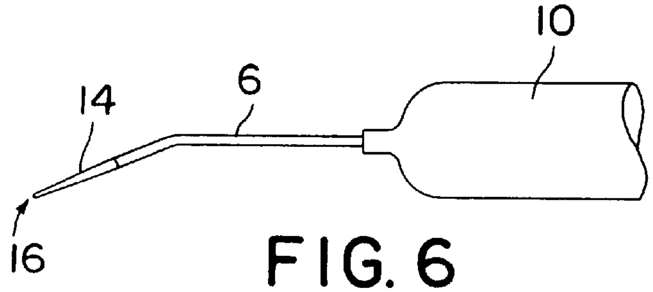
FIG. 6 is a broken view of the barrel showing an alternative embodiment of the cannula in a bent configuration that may be preferred by some users of the invention.

FIG. 6 is a broken view of the barrel 10 showing an alternative embodiment of the cannula 6 in a bent configuration that may be preferred by some users of the invention.

Figure 7:
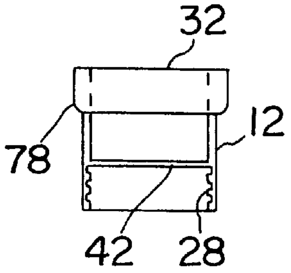
FIG. 7 is a side view of the barrel end cap of FIG. 5 showing an enlarged lateral dimension of the barrel end cap bulges of the locking hub end, used to interconnect with the check valve jaw lips.

FIG. 7 is a side view of the barrel end cap 12 of FIG. 5 showing an enlarged lateral dimension of the barrel end cap bulges 78 of the locking hub end 32. The barrel end cap bulges 78 interconnect and are tightly held as seen in FIG. 2 with the check valve jaws lips 74 disposed on the distal ends of check valve jaws 30.

Figure 8:
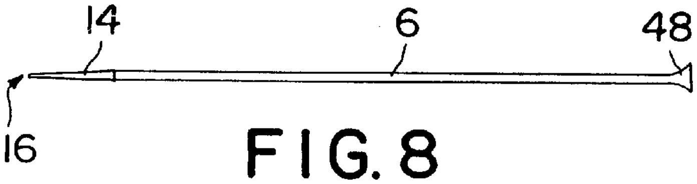
FIG. 8 is a second alternative embodiment of the cannula with a flared intake end.

FIG. 8 is a second alternative embodiment of the cannula 6 with a flared intake end 48.

Figure 9:
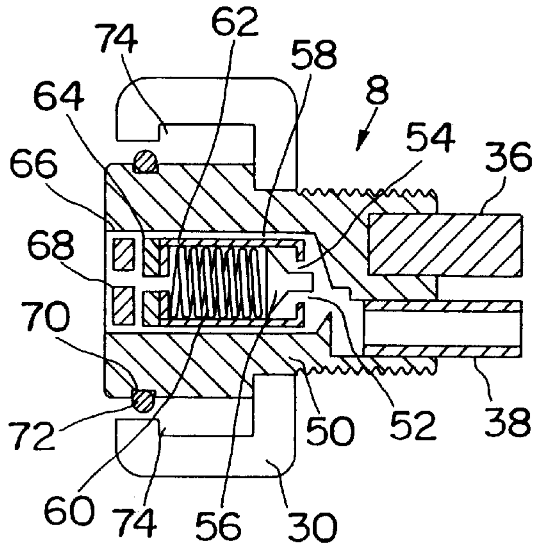
FIG. 9 is partial cross-sectional view of the double acting check valve showing the internal structure thereof.

FIG. 9 is partial cross-sectional view of the double acting check valve 8 in combination with check valve jaws 30, guide pin 36 and pneumatic pressure line connector 38 showing the internal structure of check valve 8. Double acting check valve 8 is comprised of a check valve housing 50, check valve intake manifold 52, check valve intake port 54, resilient valve shuttle 56, check valve cylinder 58, check valve biasing means 60, floating biasing means retainer 62, check valve housing cap 64, check valve assembly retainer 66, check valve discharge port 68, O-ring channel 70, O-ring 72, check valve jaws 30 and check valve jaw lips 74. Resilient valve shuttle 56 may be made from rubber, and check valve biasing means 60 is preferably a coil spring.

In operation, air pressure entering check valve 8 passes through pneumatic pressure line connector 38 into check valve intake manifold 52. The pressure is exerted on resilient valve shuttle 56 which then overcomes the resistance of the check valve biasing means 60 and opens the check valve intake port 54. The fluid then passes through the check valve cylinder 58 to emerge through the check valve discharge port 68.

When the pressure in the pneumatic pressure line connector 38 drops check valve biasing means 60 causes the resilient valve shuttle 56 to close off the check valve intake port 54 thereby preventing particulate matter from backing up into the pneumatic pressure line connector 38. Similarly in the event of an excessive pressure surge, check valve biasing means 60 will be further compressed and the top surface of resilient valve shuttle 56 will be pressed against check valve discharge port 68 thereby preventing the pressure surge from reaching fluidizing chamber 4.

Figure 10:
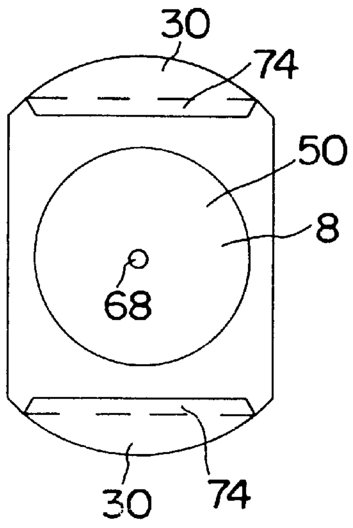
FIG. 10 is an end view of the double acting check valve and jaw, which interconnects with the locking hub end of barrel end cap as seen in FIG. 5.

FIG. 10 is an end view of the double acting check valve 8 showing the top of the check valve housing 50, check valve discharge port 68, check valve jaws 30 and check valve jaw lips 74.

Interconnection of the check valve 8 with barrel end cap 12 is achieved by inserting barrel end cap 12 into the check valve jaws 30 with the barrel end cap 12 rotationally oriented so that the check valve jaws 30 are adjacent barrel end cap flats 44. When the barrel end cap 12 has been fully inserted, the barrel end cap 12 and check valve 8 are rotated with respect to each other until the check valve jaws reach the rotation stops 46 such that check valve jaw lips 74 pass over and fully engage with barrel end cap bulges 78. See FIG. 2. Rotation stops 46 also assure that rotation is done only in the right direction and stops after there is full engagement in a twist and lock configuration. Sealing is accomplished because O-ring 72 seen in FIG. 9 comes in contact with O-ring bearing internal surfaces 80 as seen in FIG. 4.

Of course the above procedure is simply reversed when disassembly is desired. Therefore, should the prefilled, sealed, and disposable fluidizing chamber and cannula assembly run out of particulate matter before a cleaning of a patient's teeth is completed, it takes only a few seconds to disconnect the discharged fluidizing chamber and cannula assembly, dispose of it, and reconnect a prefilled replacement onto the check valve.

While the above embodiments describe using particulate matter such as aluminum oxide in the chamber, other particles such as but not limited to sodium bicarbonate can be used. Further, the above embodiments can include a separate water line running through the interior chamber from a conventional outside waterline so that water under pressure can be sprayed onto teeth in a cleaning operation while sodium bicarbonate or aluminum oxide is also used in combination to clean the teeth.

Various materials used in the construction of the embodiments include but are not limited to plastic, stainless steel, Delrin™, and Teflon™.

Referring to all the above embodiments, various components can be sealingly attached to one another by means such as but not limited to ultrasonic welding, adhesive bonding, screwing and ratcheting, and sealing by solvent welding.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended and their equivalents.

What is claimed is:

1. In an improved pressurized particulate matter delivery apparatus having a fluidizing chamber for mixing fluid and particulate matter together wherein the improvement comprises:

an inlet tube connected to a pressurized fluid source and having a discharge end disposed within the fluidizing chamber;

a cannula having an intake end disposed within the fluidizing chamber and a discharge orifice disposed outside the fluidizing chamber;

wherein the inlet tube discharge end and cannula intake end overlap each other; and a double acting check valve removably disposed between the pressurized fluid source and the fluidizing chamber to prevent backflow of particulate matter in the event of a drop in pressure from the pressurized fluid source and also to prevent a pressure surge from reaching the fluidizing chamber.

2. The apparatus of claim 1 which further comprises particulate matter disposed within the fluidizing chamber.

3. The apparatus of claim 1 in which the fluidizing chamber is comprised of a barrel and a barrel end cap, the barrel end cap having internal threads which rotate about and engage mateable threads on a top of the barrel.

4. The apparatus of claim 3 in which the inlet tube is fixedly attached to the barrel end cap and the cannula is fixedly attached to the barrel.

5. The apparatus of claim 3 in which the barrel and barrel end cap are formed of an injection moldable material, the inlet tube is insert molded into the barrel end cap and the cannula is insert molded into the barrel.

6. The apparatus of claim 1 which further comprises particulate matter disposed within the fluidizing chamber and wherein the fluidizing chamber, inlet tube, cannula and particulate matter are assembled in a manner that avoids contamination and sealed, except for inlet tube intake and cannula discharge orifice.

7. The apparatus of claim 1 in which the fluidizing chamber is comprised of a barrel and a barrel end cap, and where said apparatus further comprises:

check valve jaws connected to the check valve;

check valve jaws lips disposed on distal ends of the check valve jaws;

an O-ring groove surrounding the check valve inside the check valve jaws;

an O-ring disposed in the O-ring groove:

a locking hub end of the barrel end cap having alternating barrel end cap flats and barrel end cap bulges with rotation stops and having O-ring bearing internal surfaces;

such that the locking hub end of the barrel end cap can be inserted in between the check valve jaws along the barrel end cap flats, and rotated with respect to the check valve to the rotation stops after full insertion resulting in full engagement of the check valve jaw lips with barrel end cap bulges such that the O-ring of the check valve presses against the O-ring bearing internal surfaces of the barrel end cap to seal the barrel end cap and check valve together.

8. The apparatus of claim 7 in which the check valve further comprises:

a housing;

an intake manifold disposed within the housing;

an intake port in fluid communication with the intake manifold;

a check valve cylinder disposed within the housing and in fluid communication with the intake port;

a discharge port;

a resilient valve shuttle movably disposed within the check valve cylinder, in fluid communication with the intake port and having both the capability to selectively close off the intake port and, alternatively to selectively close off the discharge port; and a biasing means in physical communication with the resilient valve shuttle to both urge the resilient valve shuttle to close off the intake port in the absence of a predetermined pressure level pressing against resilient valve shuttle and, alternatively to yield to a pressure surge so that the resilient valve shuttle can close off the discharge port.

9. The apparatus of claim 1 in which the cannula includes a tapered nozzle.

10. The apparatus of claim 1 in which the cannula is bent.

11. The apparatus of claim 2 in which the particulate matter includes aluminum oxide.

12. The apparatus of claim 2 in which the particulate matter includes sodium bicarbonate.

13. The apparatus of claim 3 in which particulate matter disposed within the fluidizing chamber may be exhausted in use, and in which the fluidizing chamber may be recharged by the user disengaging the barrel and a barrel end cap employing the barrel end cap internal threads which counter-rotate about and disengage mateable threads on a top of the barrel, adding particulate matter into the barrel, and reingaging the internal threads of the barrel end cap with the mateable thread on the top of the barrel.

* * * * *

US006004191C1

(12) REEXAMINATION CERTIFICATE (4534th)

United States Patent

Schur et al.

(10) Number: US 6,004,191 C1

(45) Certificate Issued: Feb. 19, 2002

(54) PARTICULATE MATTER DELIVERY DEVICE

(75) Inventors: Henry B. Schur; John E. Trafton, both of Hallandale, FL (US)

(73) Assignee: Simplex Medical Systems Inc., Hallandale, FL (US)

Reexamination Request:

No. 90/005,769, Jul. 13, 2000

Reexamination Certificate for:

Patent No.: 6,004,191
Issued: Dec. 21, 1999
Appl. No.: 08/863,857
Filed: May 27, 1997

Related U.S. Application Data

(63) Continuation-in-part of application No. 08/517,379, filed on Aug. 21, 1995, now abandoned, which is a continuation-in-part of application No. 08/746,737, filed on Nov. 15, 1996, now abandoned.

(51) Int. Cl.$^{7}$ .................................................. B24C 5/04

(52) U.S. Cl. .......................................... 451/90; 451/101

(58) Field of Search ............................ 451/38, 39, 101, 451/102, 90, 99; 137/511, 535, 540, 536, 537, 538; 251/900, 337, 321

(56) References Cited

U.S. PATENT DOCUMENTS 2,133,149 A 10/1938 Poncelet
2,441,441 A 5/1948 Paasche
2,524,951 A * 10/1950 Ashton ........................ 251/144
2,577,465 A 12/1951 Jones et al.
2,641,087 A 6/1953 Greiser
2,696,669 A 12/1954 Ikse
2,725,684 A 12/1955 Crowe
2,744,361 A 5/1956 Larson et al.
3,164,153 A 1/1965 Zori
3,580,275 A * 5/1971 Hanson ................. 137/516.29
3,626,977 A * 12/1971 Riley .................... 137/516.25
3,631,631 A 1/1972 Greenstein
3,981,479 A 9/1976 Foster et al.
4,032,474 A 6/1977 Goudriaan et al.
4,174,571 A 11/1979 Gallant
4,287,812 A 9/1981 Iizumi
4,369,607 A 1/1983 Bruggeman et al.
4,475,370 A 10/1984 Stark et al.
4,646,782 A 3/1987 Ezekoye
4,673,051 A 6/1987 Darling et al.
4,941,298 A 7/1990 Fernwood et al.
4,967,791 A 11/1990 Sternberger
5,123,206 A 6/1992 Woodson
5,330,354 A 7/1994 Gallant
5,839,946 A 11/1998 Hertz
6,004,191 A 12/1999 Schur et al.

* cited by examiner

*Primary Examiner*—Robert A. Rose

(57) ABSTRACT

Disclosed is an improved apparatus for delivery of pressurized particulate matter against a surface or target to abrade, etch, erase, cut, penetrate, smooth, clean, polish and/or harden the surface or target. The most important use to which the present invention is adapted is use by dentists and oral hygienists to very effectively clean teeth, employing a particulate matter such as aluminum oxide, while at the same time having no effect on soft tissue such as the gums. This is accomplished using a prefilled, sealed, and disposable fluidizing chamber and cannula assembly that avoids contamination and which has already been approved by the FDA for dental use. Included is a fluidizing chamber having a discharge end of an inlet tube that is disposed below or overlaps the intake end of the cannula such that the discharge of the inlet tube blows the particulate matter into the fluid above the intake end of the cannula, thereby suspending it therein, without clogging. The invention further provides for a custom designed double acting safety check valve to prevent backflow of particulate matter in the event of a drop in pneumatic pressure, and also to prevent excessive pressure from reaching the fluidizing chamber and cannula in the event of a pressure surge. Another feature of the invention includes a tapered nozzle and optionally bent cannula. The check valve attaches to the pre-existing pneumatic pressure line of a dental office pedestal.

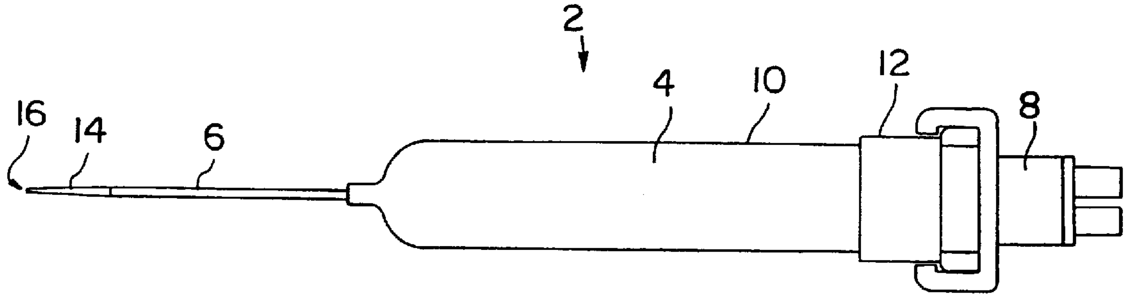

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7 and 8 is confirmed.

Claims 1–6 and 9–13 are cancelled.

New claims 14–23 and 24 are added and determined to be patantable.

*14. In an improved pressurized particulate matter delivery apparatus having a fluidizing chamber for mixing fluid and particulate matter together wherein the improvement comprises:*

*a fluidizing chamber having a barrel and a barrel end cap;*

*an inlet tube connected to a pressurized fluid source and having a discharge end disposed within the fluidizing chamber;*

*a cannula having an intake end disposed within the fluidizing chamber and a discharge orifice disposed outside the fluidizing chamber*

*wherein the inlet tube discharge end and cannula intake end overlap each other;*

*a double acting check valve removably disposed between the pressurized fluid source and the fluidizing chamber to prevent backflow of particulate matter in the event of a drop in pressure from the pressurized fluid source and also to prevent a pressure surge from reaching the fluidizing chamber, which double acting check further comprises:*

*check valve jaws connected to the check valve;*

*check valve jaws lips disposed on distal ends of the check valve jaws;*

*an O-ring groove surrounding the check valve inside the check valve jaws;*

*an O-ring disposed in the O-ring groove:*

*a locking hub end of the barrel end cap having alternating barrel end cap flats and barrel end cap bulges with rotation stops and having O-ring bearing internal surfaces;*

*such that the locking hub end of the barrel end cap can be inserted in between the check valve jaws along the barrel end cap flats, and rotated with respect to the check valve to the rotation stops after full insertion resulting in full engagement of the check valve jaw lips with barrel end cap bulges such that the O-ring of the check valve presses against the O-ring bearing internal surfaces of the barrel end cap to seal the barrel end cap and check valve together.*

*15. The apparatus of claim 14 in which the check valve further comprises:*

*a housing;*

*an intake manifold disposed within the housing;*

*an intake port in fluid communication with the intake manifold;*

*a check valve cylinder disposed within the housing and in fluid communication with the intake port;*

*a discharge port;*

*a resilient valve shuttle movably disposed within the check valve cylinder, in fluid communication with the intake port and having both the capability to selectively close off the intake port and, alternatively to selectively close off the discharge port; and*

*a biasing means in physical communication with the resilient valve shuttle to both urge the resilient valve shuttle to close off the intake port in the absence of a predetermined pressure level pressing against resilient valve shuttle and, alternatively to yield to a pressure surge so that the resilient valve shuttle can close off the discharge port.*

*16. The apparatus of claim 14 which further comprises particulate matter disposed within the fluidizing chamber.*

*17. The apparatus of claim 14 in which the fluidizing chamber is comprised of a barrel and a barrel end cap, the barrel end cap having internal threads which rotate about and engage mateable threads on a top of the barrel.*

*18. The apparatus of claim 17 in which the inlet tube is fixedly attached to the barrel end cap and the cannula is fixedly attached to the barrel.*

*19. The apparatus of claim 17 in which the barrel and barrel end cap are formed of an injection moldable material, the inlet tube is insert molded into the barrel end cap and the cannula is insert molded into the barrel.*

*20. The apparatus of claim 14 which further comprises particulate matter disposed within the fluidizing chamber and wherein the fluidizing chamber, inlet tube, cannula and particulate matter are assembled in a manner that avoids contamination and sealed, except for inlet tube intake and cannula discharge orifice.*

*21. The apparatus of claim 14 in which the cannula includes a tapered nozzle.*

*22. The apparatus of claim 14 in which the cannula is bent.*

*23. The apparatus of claim 15 in which the particulate matter includes aluminum oxide.*

*24. The apparatus of claim 15 in which the particulate matter includes sodium bicarbonate.*

* * * * *